United States Patent
Kaji

[11] Patent Number: 5,316,919
[45] Date of Patent: May 31, 1994

[54] METHOD OF PRODUCING 2 KD TO 10KD PEPTIDES HAVING NO L-METHIONINE RESIDUE

[76] Inventor: Akira Kaji, 1-1-9, Daimon-cho, Higashikurume-shi, Tokyo, Japan

[21] Appl. No.: 925,732

[22] Filed: Aug. 7, 1992

Related U.S. Application Data

[62] Division of Ser. No. 710,882, Jun. 10, 1991, Pat. No. 5,166,316.

[51] Int. Cl.$^5$ .............. A61K 37/02; C07K 5/00; C12P 21/06; C12N 1/20
[52] U.S. Cl. .................. 435/69.1; 435/320.1; 435/252.33; 435/17 H; 514/12; 530/324; 530/844
[58] Field of Search ............ 530/324, 844; 514/12; 930/170; 435/320.1, 69.1, 255, 252.33

[56] References Cited

U.S. PATENT DOCUMENTS 4,822,774  4/1989  Ito et al. ......................... 514/12

FOREIGN PATENT DOCUMENTS 0405242  2/1991  European Pat. Off. ........ C07K 7/10
1-296996 11/1989  Japan.

OTHER PUBLICATIONS

Stepein et al., Synthesis of a human insulin gene. 1983 Gene 24(2-3), 289-297.
Armah et al. (1988) Nucleic Acids Symp., Ser. No. 19, pp. 165-169.
Park et al. (1988) Abstr. Pap. Am. Chem. Soc. (196 Meet., MBTD41).
Zitomer et al. (1984) Mol. Cell Biol., vol. 4(7), pp. 1191-1197.

Primary Examiner—Robert J. Hill, Jr.
Assistant Examiner—Gian P. Wang
Attorney, Agent, or Firm—Sughrue, Mion, Zinn, Macpeak & Seas

[57] ABSTRACT

Novel peptides having pharmacologic activities, such as vasodilating, hypotensive and bronchodilating activities, and a method of making peptides are described.

4 Claims, 3 Drawing Sheets

METHOD OF PRODUCING 2 KD TO 10KD PEPTIDES HAVING NO L-METHIONINE RESIDUE

This is a divisional of application Ser. No. 07/710882 filed Jun. 10, 1991, now U.S. Pat. No. 5,166,316.

FIELD OF THE INVENTION

The invention relates to novel physiologically active peptides and a novel method of producing peptides. More particularly, the invention relates to stable peptides having pharmacologic activities, such as vasodilating, hypotensive and bronchodilating activities, and to a method of efficiently producing physiologically active peptides by recombinant DNA technology.

BACKGROUND OF THE INVENTION

A number of intestinal tract-derived peptide hormones are known. Among them, VIP (vasoactive intestinal polypeptide) is known to have favorable pharmacologic activities, for example vasodilating, hypotensive and bronchodilating activities VIP shows little variation in peptide sequence among animal species, for example, human VIP and porcine VIP are nearly identical in sequence. VIP is found not only in the intestinal tract but also in many other organs. Recently, it has become recognized that VIP may serve as a neurotransmitter.

However, because of a Met (L-methionine) residue in the molecule, naturally occurring human VIP is unstable to oxidation. Furthermore, VIP is susceptible to enzymolysis which results in inactivation. Therefore, investigations have been made on finding various derivatives of VIP that exhibit greater stability.

The present inventors made intensive investigations in an attempt to obtain peptides having naturally occurring human VIP-like activities by modifying the peptide sequence of VIP without impairing the activities of VIP and introducing one or more amino acids which would not preclude production of the peptide by recombinant DNA technology. As a result, it was found that novel peptides of the sequence:

H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-R, wherein R is Glu-Ala-OH, Glu-OH or OH (SEQ ID NOs: 1 to 3, respectively) these peptides are equal or superior to human VIP from the viewpoint of pharmacologic activity and, in addition, are stable in vivo.

Meanwhile, at present, physiologically active peptides generally are produced by extraction from natural sources, by organic synthetic means, or by utilizing recombinant DNA or genetic engineering techniques.

However, large-quantity production of physiologically active peptides with a molecular weight of 2,000 to 10,000 by extraction from animal organs or by organic chemical synthesis is not cost effective. In producing such peptides by genetic engineering techniques, when they are expressed as such in prokaryotic cells, the peptides readily decompose resulting in low recoveries. Therefore, recombinant peptides have had to be recovered by an inefficient process comprising first producing fusion proteins between the desired peptide and α-galactosidase, for instance, followed by cleavage thereof and purification of the resulting desired peptides (for example, Simoncsits et al, *Eur. J. Biochem.*, vol 178, pp 343-350 (1988) and JP-A-01-296996 (The term "JP-A" as used herein means an "unexamined published Japanese patent application")).

The present inventors made intensive investigations on the production method of gene manipulation and found that large-quantity production of L-methionine-free peptides with a molecular weight of 2,000 to 10,000 becomes possible when a fused protein composed of a fragment of the galK protein, which fragment covers 200 to 300 amino acid residues from the N terminus of said protein, and any of the above-mentioned peptides having a molecular weight of 2,000 to 10,000 as coupled to said fragment at the C terminus thereof via a L-methionine residue, can be expressed in prokaryotic cells using the trp promoter. The fused protein is purified, treated with cyanogen bromide and said peptide, 2,000 to 10,000 in molecular weight, is purified from the resulting peptide mixture.

SUMMARY OF THE INVENTION

The invention thus provides:

(1) Novel peptides having the sequence:
H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-R, wherein R is Glu-Ala-OH, Glu-OH or OH (SEQ ID NOs: 1 to 3, respectively), (said peptides are hereinafter referred to as compounds of the invention), and (2) A novel method of producing a peptide having no L-methionine residue in their molecule and having a molecular weight of 2,000 to 10,000, which method comprises:

(A) expressing in prokaryotic cells using a trp promoter a fused protein comprising:
(1) a fragment of the galK protein which corresponds to 200 to 300 amino acid residues from the N terminus of said protein, and
(2) an L-methionine-free peptide which have a molecular weight of 2,000 to 10,000 coupled to said galK protein fragment at the C terminus thereof via a L-methionine residue;

(B) purifying said fused protein;

(C) cleaving said purified fused protein with cyanogen bromide to give a peptide mixture; and (D) isolating peptides which have a molecular weight of 2,000 to 10,000 from the peptide mixture to obtain said L-methionine-free peptide.

DETAILED DESCRIPTION OF THE INVENTION

Figure 1:
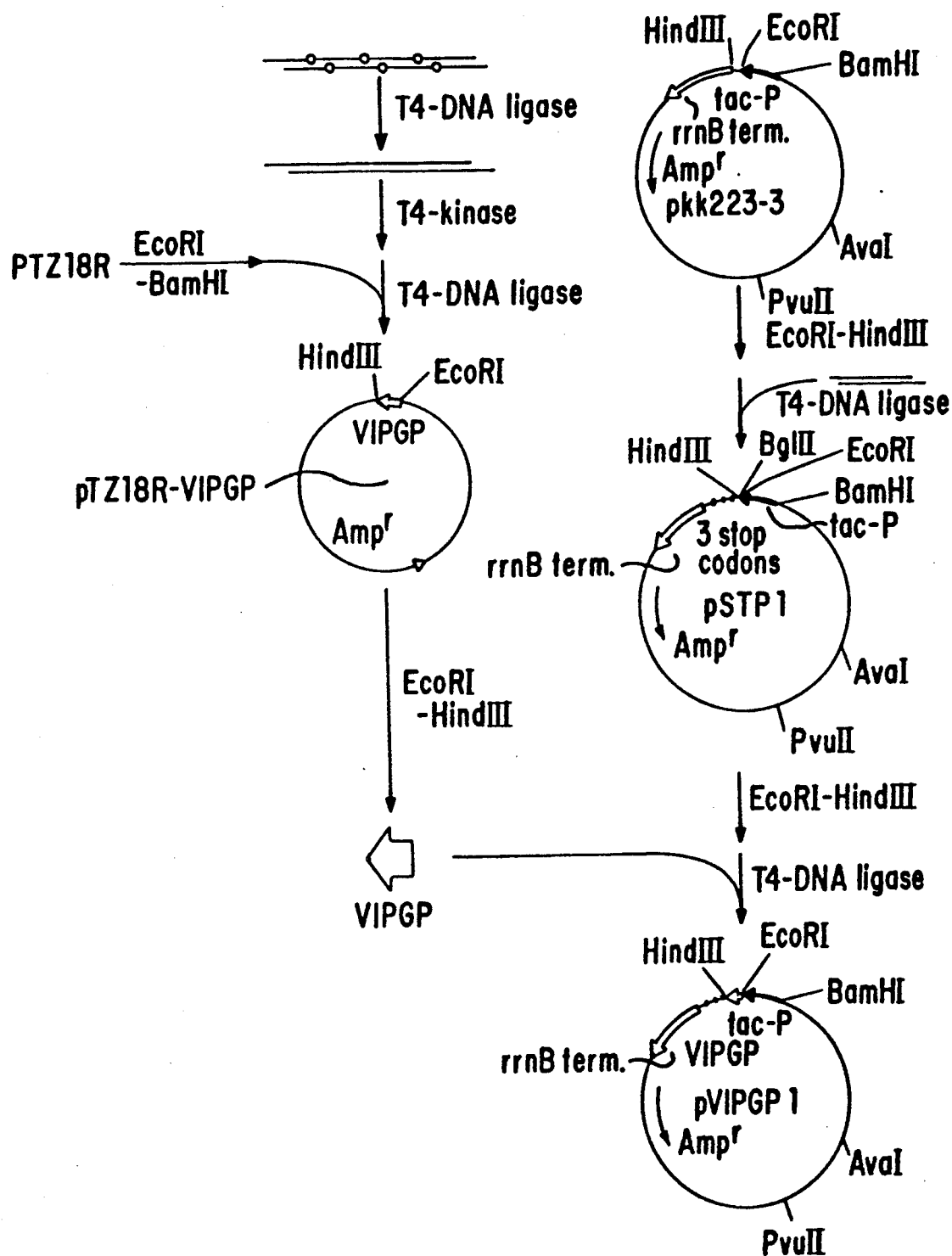
FIG. 1 shows the structures of the plasmids pSTP 1, and pVIPGP1 to which the synthesized gene VIPGP is inserted.

In the sequences of the compounds of the invention as given above and in the description which follows, His stands for the L-histidine residue and, similarly, Ser for L-serine, Asp for L-aspartic acid, Ala for L-alanine, Val for L-valine, Phe for L-phenylalanine, Thr for L-threonine, Asn for L-asparagine, Tyr for L-tyrosine, Arg for L-arginine, Leu for L-leucine, Lys for L-lysine, Gln for L-glutamine, Ile for L-isoleucine, Gly for glycine, Pro for L-proline and Glu for L-glutamic acid.

The compounds of the invention may be produced by any general liquid-phase or solid-phase organic synthetic process for producing peptides. It is advantageous, however, to produce them by the recombinant DNA technology using, for example, *Escherichia coli.*

Mention is now made of the organic synthesis of the novel peptides of the invention.

The compounds of the invention can be synthesized by any of the conventional processes generally used for condensation of amino acids, such as the solid-phase or liquid-phase method. An example is described below.

The compounds of the invention can be obtained by using, as a starting material, a tert-butoxycarbonyl-L-amino acid (hereinafter, Boc-amino acid)-coupled 4-(hydroxymethyl)phenylacetamidomethyl resin, which may be obtained from a commercial source or prepared by coupling a Boc-amino acid to a 4-(hydroxymethyl)-phenylacetamidomethyl resin. In either case, the Boc-amino acid must correspond to the N-terminal amino acid. Boc-amino acids, whose amino group, carboxyl group and/or hydroxyl group is protected as necessary, are successively coupled to the resin-bound amino acid or peptide in accordance with the desired sequence. The thus-produced crude final product is then purified.

Appropriate protective groups for the amino, imino, carboxyl and hydroxyl groups include, among others, p-toluenesulfonyl and 2-chlorobenzyloxycarbonyl for the amino or imino group, $\beta$-cyclohexyl and $\gamma$-benzyl for the carboxyl group, and benzyl and 2,6-dichlorobenzyl for the hydroxyl group.

The compounds of the invention can be used in the form of injections. In producing injectable preparations, distilled water for injection, physiologic saline, aqueous dextrose solution, vegetable oils for injection, propylene glycol, polyethylene glycol and the like can be used as diluents. The preparations may further contain, as necessary, isotonizing agents, stabilizers, preservatives, soothing agents etc. in appropriate amounts.

The compounds of the invention can also be administered directly to the nasal mucosa and/or bronchus by means of a nebulizer or inhaler or the like.

The compounds of the invention may also be used in the form of external preparations, together with penetration promoters and so forth.

Furthermore, the compounds of the invention can be used in the form of salts with pharmacologically acceptable acids or bases.

In the following, a novel method of producing physiologically active peptides is described in more detail. When this method is used, the compounds of the invention can be obtained more efficiently.

Although the novel method of the invention for peptide production requires synthesis of structural genes which do not occur naturally, any structural gene as desired can be constructed, according to known methods of Tanaka et al, *Nucleic Acids Research,* vol. 11 (6), pp. 1707–1723 (1983) or Itakura et al, *Science,* vol. 198, pp. 1056–1063 (1977). Further, the structural gene as desired can be efficiently constructed by selecting DNA sequences most highly or frequently utilized in *Escherichia coli* from among the sequences coding for amino acids constituting the desired peptide and by designing the gene so that regions rich in A-T base pairs might not be in succession, so that the synthetic fragments to serve as parts for synthesizing the structural gene might be free of any intramolecular self-complementary base sequences or of any repeating sequences and might be about 30 bases in length.

A desired plasmid can be obtained by inserting the thus-obtained structural gene into a conventional plasmid for expression in prokaryotic cells together with the galK protein (galactokinase) fragment gene and the trp promoter disposed upstream from the latter gene so that said structural gene might occur downstream from said galK protein fragment gene. As the conventional plasmid, pBR plasmids and pUC plasmids are preferred. Among them, pUC plasmids are more preferred since it is not necessary to use indoleacrylic acid (IAA) with them.

The microorganism to be transformed may be a derivative of *Escherichia coli* K12, such as *Escherichia coli* RR1$\Delta$M15 (ATCC 35102), JM101 or JM105. Strains requiring no amino acids, such as *Escherichia coli* W3110 (IFO 12713), are more preferred, however.

For peptide production by culturing, conventional culture processes may be used with such media as L medium, M9 medium, M9-casamino acids medium a high-concentration phosphate medium and high-concentration phosphate-casamino acids medium. When a pBR plasmid is used, culture in the presence of indoleacrylic acid (IAA) can give the fused protein in large quantities. In that case, the so-called fed-batch fermentation (see Fieschko et al, *Chem. Eng. Commun.,* vol. 45, pp 229–240 (1986)) is preferred wherein the concentrations of nutrients (N, O and C) and growth-inhibitors (acetates) are controlled at a suitable level to thereby provide high-density cultures with a smaller quantity of medium.

The fused protein expressed in *Escherichia coli* can be isolated as a water-insoluble fraction by disruption of *Escherichia coli* cells by sonication followed by centrifugation to thereby separate the fused protein from most water-soluble proteins in *Escherichia coli* cells.

For excising the desired peptide from the fused protein, the fused protein purified in the above manner is cleaved at the Met site thereof using cyanogen bromide.

The peptide mixture resulting from the above cleavage of the fused protein is subjected to cation exchange chromatography and reverse-phase chromatography whereby the compound of the invention can be purified from said peptide mixture.

The compounds of the invention obtained in the above manner can be identified by amino acid composition analysis, amino acid sequence analysis by Edman degradation and immunoassay with anti-VIP antibody.

Some typical organic synthetic processes for the production of the compounds of the invention are illustrated in the following reference examples.

REFERENCE EXAMPLE 1

A Boc-L-alanine-bound 4-(hydroxymethyl)-phenylacetamidomethyl resin (mfd. by Applied Biosystems Co.) (0.5 mmol) was treated with 50% trifluoroacetic acid in methylene chloride for elimination of the Boc group. Then, 2 mmol of O-benzyl-Boc-L-glutamic acid (mfd. by Applied Biosystems Co.) was subjected to coupling to the deprotected resin using dicyclohexylcarbodiimide.

Then, peptide chain extension was carried out in the same manner using Boc-amino acids in the following order: Pro, Gly, Asn, Leu, Ile, Ser, Asn, Leu, Tyr, Lys, Lys, Val, Ala, Leu, Gln, Lys, Arg, Leu, Arg, Thr, Tyr, Asn, Asp, Thr, Phe, Val, Ala, Asp, Ser, and His.

For the above reaction procedure, a peptide synthesizer (model 430A, mfd. by Applied Biosystems Co.) was used.

After completion of the final coupling reaction, the resin was treated with hydrofluoric acid in the presence of anisole and ethyl methyl sulfide at −20° C. for 30 minutes and then at 0° C. for 10 minutes for deprotection and release from the resin. The product was dissolved in 2N acetic acid and, after lyophilization, purified by reversed-phase high-performance liquid chromatography (HPLC) to give 40 mg of H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-Glu-Ala-OH (SEQ ID NO: 1) as a white powder.

REFERENCE EXAMPLE 2

A O-benzyl-Boc-L-glutamic acid-coupled 4-(hydroxymethyl)phenylacetamidomethyl resin (mfd. by Applied Biosystems Co.) (0.5 mmol) was treated with 50% trifluoroacetic acid in methylene chloride for elimination of the Boc group and then 2 mmol of Boc-L-proline (mfd. by Applied Biosystems Co.) was subjected to coupling to said resin using dicyclohexylcarbodiimide.

Peptide chain extension was then conducted in the same manner using Boc-amino acids in the following order: Gly, Asn, Leu, Ile, Ser, Asn, Leu, Tyr, Lys, Lys, Val, Ala, Leu, Gln, Lys, Arg, Leu, Arg, Thr, Tyr, Asn, Asp, Thr, Phe, Val, Ala, Asp, Ser, and His.

For the above reaction procedure, a peptide synthesizer (model 430A, mfd. by Applied Biosystems Co.) was used.

The final reaction mixture was treated in the same manner as in Reference Example 1 to give 50 mg of H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-Glu-OH (SEQ ID NO: 2) as a white powder.

REFERENCE EXAMPLE 3

A Boc-L-proline-coupled 4-(hydroxymethyl)-phenylacetamidomethyl resin (mfd. by Applied Biosystems Co.) (0.5 mmol) was treated with 50% trifluoroacetic acid in methylene chloride for elimination of the Boc group and then 2 mmol of Boc-glycine (mfd. by Applied Biosystems Co.) was subjected to coupling to the L-proline-coupled resin using dicyclohexylcarbodiimide.

Further chain extension was effected using Boc-amino acids in the following order: Asn, Leu, Ile, Ser, Asn, Leu, Tyr, Lys, Lys, Val, Ala, Leu, Gln, Lys, Arg, Leu, Arg, Thr, Tyr, Asn, Asp, Thr, Phe, Val, Ala, Asp, Ser, and His.

For the above reaction procedure, a peptide synthesizer (model 430A, mfd. by Applied Biosystems Co.) was used.

The final reaction mixture was treated in the same manner as in Reference Example 1 to give 50 mg of H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-OH (SEQ ID NO: 3) as a white powder.

The structure, namely amino acid sequence, of each of the peptides produced in the above manner was identified by reversed-phase HPLC of phenylthiohydantoin (PTH)-amino acids resulting from Edman degradation using a peptide sequencer (model 477A, mfd. by Applied Biosystems Co.).

The following examples illustrate the compounds of the invention and the method of peptide production according to the invention.

EXAMPLE 1

Effects on the blood pressure in rats

Two of the compounds of the invention were each administered to male ICR mice of 5 weeks of age by injection into the caudal vein at a dose of 40 μg/kg. At 5, 10, 20 and 30 minutes after administration, the caudal vein blood pressure was measured using a noninvasive sphigmomanometer (TK-150). The results obtained are shown in Table 1.

TABLE 1

| | 5 min | 10 min | 15 min | 20 min |
|---|---|---|---|---|
| Peptide of Reference Example 1 (SEQ ID NO: 1) | 71.1% | 66.4% | 74.9% | 77.9% |
| Peptide of Reference Example 3 (SEQ ID NO: 3) | 58.9% | 74.1% | 94.3% | 105.5% |
| Naturally occurring VIP | 83.3% | 97.2% | 95.9% | 102.8% |
| Physiological saline | 100% | 100% | 100% | 100% |

As shown in Table 1, the reduction in blood pressure after administration of the peptides of the present invention was greater than that after administration of naturally occurring VIP when compared with the caudal vein blood pressure after administration of physiological saline, taken as 100%, indicating their potent hypotensive activity. In addition, the activity was of long duration. The peptides of the invention have therapeutic utility.

REFERENCE EXAMPLE 4

The following procedures were conducted to obtain the plasmids of pSTP1 and pVIPGP1, which were shown in FIG. 1.

i) Synthesis of fragments

The eight fragments specified below were synthesized by the solid-phase phosphoramidite method using a DNA synthesizer (model 380A mfd. by Applied Biosystems Co.)

| | |
|---|---|
| 1) 5'-AATTCATGCACTCTGACG | (SEQ ID NO: 4) |
| 2) 5'-CAGTGAATACAGCGTCAGAGTGCATG | (SEQ ID NO: 5) |
| 3) 5'-CTGTATTCACTGACAACTACACTCGTC | (SEQ ID NO: 6) |
| 4) 5'-TGTTTACGCAGACGAGTGTAGTTGT | (SEQ ID NO: 7) |
| 5) 5'-TGCGTAAACAGCTGGCAGTTAAG | (SEQ ID NO: 8) |
| 6) 5'-TCAGGTATTTCTTAACTGCCAGC | (SEQ ID NO: 9) |
| 7) 5'-AAATACCTGAACTCTATCCTGAACGGTCCGGA | (SEQ ID NO: 10) |
| 8) 5'-AGCTTCCGGACCGTTCAGGATAGAGT | (SEQ ID NO: 11) |

For purification of the above fragments, each ammonia solution obtained after completion of solid-phase synthesis on a DNA synthesizer and containing an oligonucleotide protected on the bases and on the 5' hydroxyl group was heated at 55° C. for 5 hours to eliminate the protective groups on bases, then the ammonia was distilled off under reduced pressure and the residue was subjected to reversed-phase HPLC to give a fraction comprising the oligonucleotide protected only at the 5' hydroxyl group. The fraction obtained was treated with 80% acetic acid at room temperature for 15 to 30 minutes for elimination of the protective group on the 5' hydroxyl group, the cetic acid was distilled off under reduced pressure and the residue was applied to an anion exchange column (DEAE-2sw) to give an oligonucleotide fraction. The fraction was desalted on a gel filtration column (Sephadex G25) to give the desired fragment.

ii) Phosphorylation

The fragments 2) to 7) shown above were phosphorylated. Thus, 800 pmol of each fragment were added to a mixed solution (buffer 1) composed of 60 mM Tris hydrochloride buffer (pH 7.5), 10 mM $MgCl_2$, 15 mM 2-mercaptoethanol and 0.08 mM ATP and, after further addition of 25 units of T4 kinase (mfd. by BRL Co.), the reaction was conducted at 37° C for 2.5 hours. Then, the reaction mixture was heated at 65° C to 15 minutes to inactivate the enzyme. A half volume each of the six reaction mixtures and 800 pmol each of the oligonucleotide fragments 1) and 8) were mixed and collectively desalted on a gel filtration column (Sephadex G50).

iii) Ligation of the fragments

The desalted fraction was concentrated on a centrifugal concentrator, 25 μl of a buffer comprising 50 mM Tris-hydrochloride buffer (pH 7.6) and 10 mM $MgCl_2$ was further added to the concentrate, the mixture was heated at 90° C. for 3 minutes and then gradually cooled for annealing. After cooling, dithiothreitol was added to a concentration of 20 mM to the reaction mixture, followed by further addition of ATP to a concentration of 1 mM. Ligation was then carried out at 16° C. for 22 hours using 875 units of T4 DNA ligase (mfd. by Takara Co.). The enzyme was then inactivated by heating at 65° C. for 15 minutes.

iv) Purification

The reaction mixture was subjected to polyacrylamide gel electrophoresis (PAGE) (8% polyacrylamide, 2 mm gel thickness). A band in a position corresponding to the desired length (100 bp) was excised and the DNA was electrically transferred to NA-45 paper (mfd. by S&S Co.) for adsorption thereon. Elution was effected by heating the paper in a high salt concentration buffer comprising 1 M NaCl, 20 mM Tris-hydrochloride buffer (pH 8.0) and 0.1 mM EDTA at 65° C. for 50 minutes. The eluate solution was treated with phenol, phenol-chloroform and chloroform to remove impurities and, then, 2.5 volumes of ethanol were added to the solution for precipitation of the DNA.

v) Phosphorylation

The thus-obtained gene, not phosphorylated at the 5' end, was added to a mixed solution composed of 60 mM Tris-hydrochloride buffer (pH 7.5), 10 mM $MgCl_2$, 15 mM 2-mercaptoethanol and 0.08 mM ATP. After further addition of 62.5 units of T4 kinase (mfd. by BRL Co.), the reaction was carried out at 37° C. for 2.5 hours. After enzyme inactivation by heating at 65° C. for 15 minutes, the reaction mixture was desalted on a gel filtration column (Sephadex G50) to give a gene (gene 1).

Separately, 30 μg of the plasmid pTZ18R were added to a mixed solution comprising 10 mM Tris-hydrochloride buffer (pH 7.5), 10 mM $MgCl_2$, 1 mM dithiothreitol and 100 mM NaCl, 450 units of the restriction enzyme EcoRI and 400 units of the restriction enzyme HindIII were added to the resultant mixture and the reaction was conducted at 37° C. for 2.5 hours. For separation, the reaction mixture was subjected to 0.7% low-melting-point agarose gel electrophoresis, a band of about 2.9 kb was excised, the excised gel was melted by heating at 65° C. for 5 minutes, phenol was added and the resultant mixture was centrifuged. The upper layer was stirred with phenol-chloroform and with chloroform, each time followed by centrifugation. Ethanol precipitation was carried out by adding 3 M sodium acetate (one-tenth volume) and ethanol (2.5 volumes) to the final upper layer to give a DNA fragment [pTZ18R(E-H)].

The gene 1 (11 ng) was joined to pTZ18R(E-H) (300 ng) by conducting the reaction in a ligation buffer at 16° C. for 19.5 hours using 350 units of T4 DNA ligase to give a reaction mixture containing a plasmid (pTZ18R-gene 1). *Escherichia coli* RR1ΔM15 was transformed with said reaction mixture by the conventional $CaCl_2$ method. A transformant was isolated as a white colony on an L plate containing 50 μg/ml of ampicillin.

A single-stranded DNA was extracted from the thus-obtained transformant by a conventional method and its base sequence was identified by the dideoxy method. A plasmid (pTZ18R-VIPGP) containing the gene fragment (VIPGP)

| | |
|---|---|
| AATTCATGCACTCTGACGCTGTATTCACTGACAACTACACTCGTCTGCGTAAACAGCTGG- | |
| GTACGTGAGACTGCGACATAAGTGACTGTTGATGTGAGCAGACGCATTTGTCGACC- | |
| CAGTTAAGAAATACCTGAACTCTATCCTGAACTGATAG | (SEQ ID NO: 12) |
| GTCAATTCTTTATGGACTTGAGATAGGACTTGACTATCCTAG | (SEQ ID NO: 13) |
| (VIPGP) | | was thus identified as the desired plasmid containing the gene 1. The transformant harboring said plasmid was designated as *Escherichia coli* RR1ΔM15(pTZ18R-VIPGP).

vi) Vector preparation

The plasmid pKK223-3 (obtained from Pharmacia Co.; 3 μg) was added to a mixed solution comprising 10 mM Tris-hydrochloride buffer (pH 7.5), 10 mM $MgCl_2$, 1 mM dithiothreitol and 100 mM NaCl. To the mixture were further added 42 units of the restriction enzyme EcoRI and 60 units of the restriction enzyme HindIII. The digestion reaction was carried out at 37° C. for 2 hours and 40 minutes. The reaction mixture was subjected to 0.7% low-melting-point agarose gel electrophoresis for DNA separation. A band of about 4.5 kb was excised, the gel was melted by heating at 65° C. for 5 minutes, phenol was added to the melt and the resultant mixture was centrifuged. The upper layer was stirred with phenol-chloroform and with chloroform, each time followed by centrifugation. Ethanol precipitation was effected by adding one-tenth volume of 3 M sodium acetate and 2.5 volumes of ethanol to the final upper layer to give a DNA fragment [pKK223-3(E-H)].

pKK223-3(E-H) (100 ng) was reacted with 6.7 ng of the DNA fragments

| 9) 5'-AATTCAGATCTCAAGCTTAAGTGACTAG | (SEQ ID NO: 14) |
| 10) 5'-AGCTCTAGTCACTTAAGCTTGAGATCTG | (SEQ ID NO: 15) |

(containing three codons shifted in reading frame; prepared in advance on a DNA synthesizer) in a ligation buffer at 16° C. for 17 hours using 350 units of T4 DNA ligase. This reaction mixture was used to transform *Escherichia coli* RR1ΔM15 by the conventional CaCl$_2$ method and a transformant was obtained on an L-plate containing 50 μg/ml of ampicillin.

A plasmid (pSTP1) was extracted from the thus-obtained transformant by the alkaline lysis method. The plasmid was added to a mixed solution comprising 10 mM Tris-hydrochloride buffer (pH 7.5), 10 mM MgCl$_2$, 1 mM dithiothreitol and 100 mM NaCl and treated with the restriction enzyme EcoRI, HindIII or BglI. Each enzyme treatment resulted in cleavage only at one site. The recombinant was thus identified as the desired one and designated as *Escherichia coli* RR1ΔM15(pSTP1).

About 2 μg of the plasmid pSTP1 was added to a mixed solution comprising 10 mM Tris-hydrochloride buffer (pH 7.5), 10 mM MgCl$_2$, 1 mM dithiothreitol and 100 mM NaCl After further addition of 56 units of the restriction enzyme EcoRI and 50 units of the restriction enzyme HindIII, the reaction was conducted at 37° C. for 2 hours. The reaction mixture was subjected to 0.7% low-melting-point agarose gel electrophoresis for DNA separation. The desired gel band was excised and melted by heating at 65° C. for 5 minutes, phenol was added and the mixture was centrifuged. The upper layer was stirred with phenol-chloroform and then with chloroform, each time followed by centrifugation. Ethanol precipitation was effected by adding one-tenth volume of 3 M sodium acetate and 2.5 volumes of ethanol to the final upper layer to give a DNA fragment [pSTP1(E-H)].

Separately, about 2 μg of the plasmid pTZ18R-VIPGP was added to a mixed solution comprising 10 mM Tris-hydrochloride buffer (pH 7.5), 10 mM MgCl$_2$, 1 mM dithiothreitol and 100 mM NaCl and, after further addition of 56 units of the restriction enzyme EcoRI and 50 units of the restriction enzyme HindIII, the digestion reaction was conducted at 37° C. for 2 hours. The reaction mixture was subjected to 3% low-melting-point agarose gel electrophoresis for separation. The desired gel band was excised and melted by heating at 65° C. for 5 minutes, phenol was added and the mixture was centrifuged. The upper layer was stirred with phenol-chloroform and with chloroform, each time followed by centrifugation. To the final upper layer were added one-tenth volume of 3 M sodium acetate and 2.5 volumes of ethanol for ethanol precipitation to give a DNA fragment (VIPGP).

About 50 ng of pSTP1(E-H) and about 10 ng of VIPGP were added to a mixed solution comprising 50 mM Tris-hydrochloride buffer (pH 7.5), 10 mM MgCl$_2$, 10 mM dithiothreitol, 25 mM NaCl and 1 mM ATP. After further addition of 175 units of T4 DNA ligase, the ligation reaction was carried out at 16° C. for 18 hours. The ligation mixture was used to transform *Escherichia coli* RR1ΔM15 in the conventional manner by the CaCl$_2$ method to give a transformant.

The plasmid was extracted from the thus-obtained transformant by the alkaline lysis method, then added to a mixed solution comprising 10 mM Tris-hydrochloride buffer (pH 7.5), 10 mM MgCl$_2$, 1 mM dithiothreitol and 100 mM NaCl and cleaved with the restriction enzymes EcoRI and HindIII, whereby a 100 bp gene 1 was obtained. Treatment with BglI failed to cleave the plasmid, while treatment with PvuII resulted in cleavage at two sites. These facts confirmed that the desired recombinant carrying one VIPGP gene had been obtained. The transformant was designated as *Escherichia coli* RR1ΔM15(pVIPGP1).

EXAMPLES 2 TO 5

(1) Recombinant preparation

Preparation of pGMVG1/RR1ΔM15

The plasmid pVIPGP1 obtained in Reference Example 4 (3 μg) was dissolved in high-salt-concentration buffer [10 mM Tris-hydrochloride (pH 7.5), 10 mM MgCl$_2$, 1 mM dithiothreitol (DTT) and 100 mM NaCl], 40 units of the restriction enzyme EcoRI and 40 units of the restriction enzyme SspI were added to the solution and the digestion reaction was conducted at 37° C. for 2 hours. The reaction mixture was subjected to 1% agarose gel electrophoresis for separation. A band of about 0.6 kb was subjected to DNA transfer to NA-45 paper (mfd. by S&S Co.) for DNA adsorption on said paper. The paper was warmed at 65° C. for 30 minutes in DNA extraction buffer [1 M NaCl, 20 mM Tris-hydrochloride (pH 8.0) and 0.1 mM EDTA] for DNA fragment extraction. The extract solution was stirred with phenol and then with chloroform, each time followed by centrifugation. The final upper layer was desalted on Sephadex G-25

The thus-obtained DNA fragment was treated with 1 unit of Klenow fragment at 37° C. for 40 minutes in Klenow buffer [50 mM Tris-hydrochloride (pH 7.2), 10 mM MgSO$_4$, 0.1 mM DTT, 50 μg/ml bovine serum albumin (BSA) and 0.2 mM dNTP]. The reaction mixture was then heated at 65° C. for 15 minutes for enzyme inactivation and then desalted on Sephadex G-50 to give a fragment, pVIPGP1(E-Ss-Klenow).

The plasmid pDR540 (obtained from Pharmacia Co.; 2 μg) was dissolved in high-salt-concentration buffer [10 mM Tris-hydrochloride (pH 7.5), 10 mM MgCl$_2$, 1 mM DTT and 100 mM NaCl], 50 units of the restriction enzyme MluI was added to the solution and the reaction was carried out at 37° C. for 2 hours. The reaction mixture was heated at 65° C. for 15 minutes for enzyme inactivation and then desalted on Sephadex G-50. The thus-obtained DNA fragment was treated with 1 unit of Klenow fragment at 30° C. for 30 minutes in Klenow buffer [50 mM Tris-hydrochloride (pH 7.2), 10 mM MgSO$_4$, 0.1 mM DTT, 50 μg/ml BSA and 0.2 mM dNTP]. The DNA fragment was desalted on Sephadex G-50.

The DNA fragment obtained was treated with 1 unit of alkaline phosphatase in alkaline phosphatase buffer [50 mM Tris-hydrochloride (pH 8.0) and 0.1 mM EDTA] at 37° C. for 1 hour. Phenol was added to the reaction mixture and the whole mixture was stirred for enzyme inactivation. The upper layer after centrifugation was further stirred with chloroform, followed by centrifugation, whereby phenol elimination was attained. To the upper layer were added one-tenth volume of 3 M sodium acetate and 2.5 volumes of ethanol.

By the ethanol precipitation, the fragment pDR540(M-Klenow-Alp) was purified.

Both the DNA fragments prepared, namely the pVIPGP1(E-Ss-Klenow) fragment (36 ng) and the pDR540(M-Klenow-Alp) fragment (90 ng), were subjected to ligation in ligation buffer [66 mM Tris-hydrochloride (pH 7.6), 6.6 mM MgCl$_2$, 10 mM DTT and 0.1 mM ATP] at 16° C. for 20 hours using 350 units of T4 DNA ligase. The ligation mixture was used to transform *Escherichia coli* RR1ΔM15 in the conventional manner by the Hanahan method. The desired transformant of Example 2, pGMVG1/RR1ΔM15 was obtained on an L-plate containing 50 μg/ml of ampicillin. The directionality of the inserted gene was confirmed by analyzing the HindIII cleavage pattern.

Figure 2:
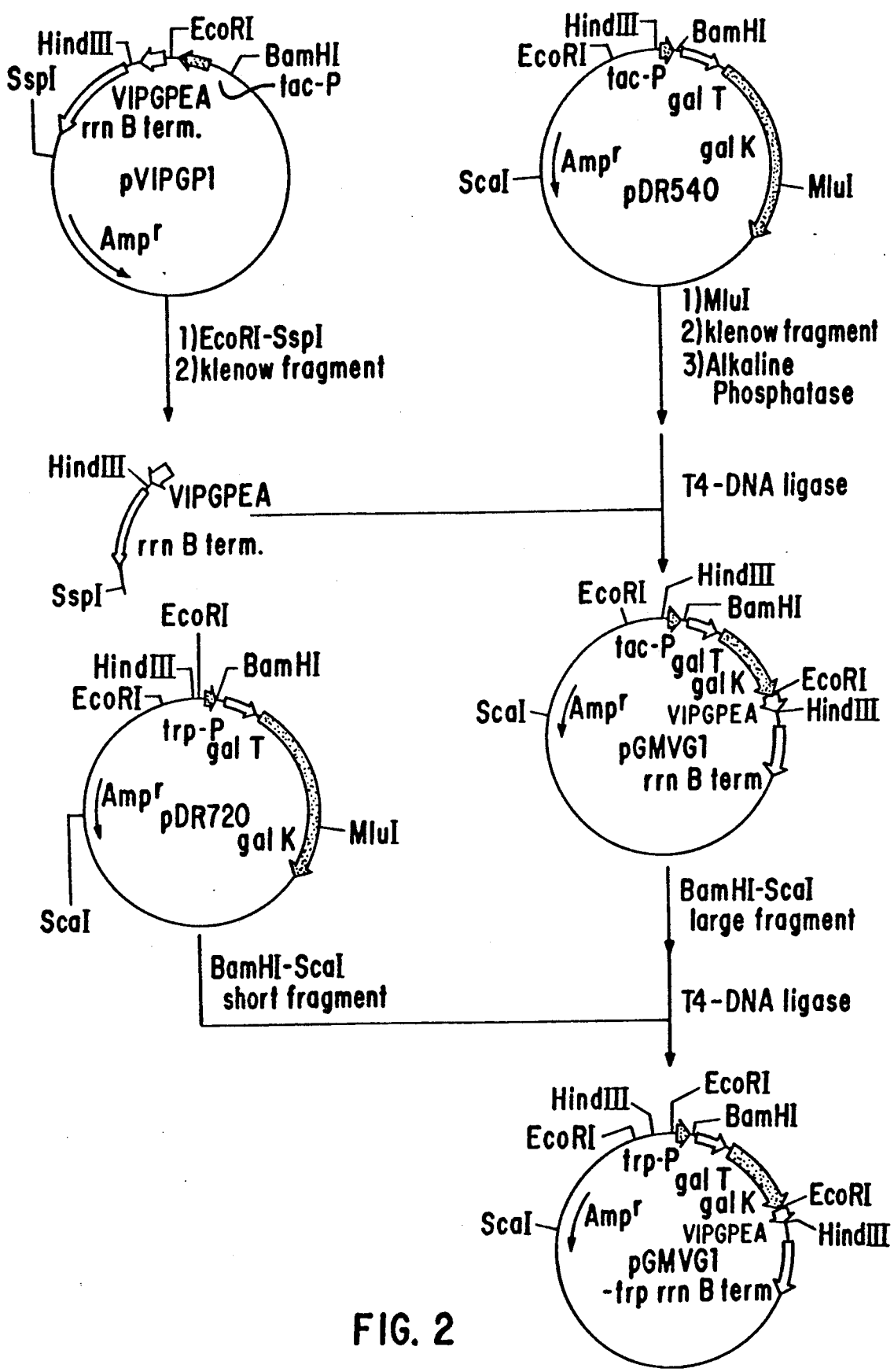
FIG. 2 shows the structure of the plasmid which codes the fused protein galK-VIPGPEA.

The structure of the plasmid pGMVG1 is illustrated in FIG. 2. The plasmid was constituted by incorporation of the DNA fragment which was essentially consisting of VIPGPEA-coading gene and rrn B terminater into the MluI portion of the plasmid pDR540. Therefore, the plasmid coded the fused protein consisting of the fragment with 266 amino acid residues of the galK protein fragment with 264 amino acids and the restriction enzyme portion with 2 amino acids, and VIPGPEA coupled to the fragment at the C terminals thereof via a L-methioanine residue, with the expression thereof being controlled by a tac promoter.

Preparation of pGMVG1-trp/C600galK⁻

The plasmid pGMVG1 (2 μg) obtained Example 2 was dissolved in high-salt-concentration buffer [10 mM Tris-hydrochloride (pH 7.5), 10 mM MgCl$_2$, 1 mM DTT and 100 mM NaCl], 50 units of the restriction enzyme BamHI and I00 units of the restriction enzyme ScaI were added to the solution and the reaction was conducted at 37° C. for 75 minutes. The reaction mixture was subjected to 0.7% low-melting-point agarose gel electrophoresis for separation and a band of about 3.5 kb was excised. The gel fragment was melted by heating at 65° C. for 5 minutes, phenol was added, the mixture was stirred and centrifuged, the upper layer was further stirred with phenol-chloroform and then with chloroform, each time followed by centrifugation. Ethanol precipitation was effected by adding one-tenth volume of 3 M sodium acetate and 2.5 volumes of ethanol to the final upper layer to give the desired pGMVG1(E-Sc) fragment.

Separately, 2 μg of the plasmid pDR720 (obtained from Pharmacia Co.) were dissolved in high-salt-concentration buffer [10 mM Tris-hydrochloride (pH 7.5), 10 mM MgCl$_2$, 1 mM DTT and 100 mM NaCl], 40 units of the restriction enzyme BamHI and 80 units of the restriction enzyme ScaI were added and the reaction was conducted at 37° C. for 70 minutes. The reaction mixture was subjected to 0.7% low-melting-point agarose gel electrophoresis for separation and a band of about 0.9 kb was excised. The gel fragment was melted by heating at 65° C. for 5 minutes, phenol was added, the mixture was stirred and then centrifuged. The upper layer was further stirred with phenol-chloroform and with chloroform, each time followed by centrifugation. To the final upper layer were added one-tenth volume of 3 M sodium acetate and 2.5 volumes of ethanol for ethanol precipitation, which gave the desired pDR720(E-Sc) fragment.

The two DNA fragments prepared in the above manner, namely the pGMVG1(E-Sc) fragment (20 ng) and the pDR720(E-Sc) fragment (100 ng), were subjected to ligation in ligation buffer [66 mM Tris-hydrochloride (pH 7.6), 6.6 mM MgCl$_2$, 10 mM DTT and 0.1 mM ATP] at 16° C. for 24 hours using 700 units of T4 DNA ligase. The ligation mixture was used to transform *Escherichia coli* C600galK⁻ in the conventional manner by the Hanahan method. The desired transformant of Example 3, pGMVG1-trp/C600galK⁻ was obtained on an L-plate containing 50 μg/ml of ampicillin and 2.5 μg/ml of tryptophan. The gene insertion was confirmed by cleavage with the restriction enzymes HindIII and PstI.

The structure of the plasmid pGMVG1-trp is illustrated in FIG. 2. The plasmid was constituted by substituting the promoter region of the plasmid pDR720 for that of the plasmid pGMVG1. Therefore, the expression of the fused protein was controlled by a trp promoter.

Preparation of pGMVGH1-trp/C600galK⁻ i) Preparation of pUCSTP1

The plasmid pSTP1 obtained in Reference Example 4 (5 μg) was dissolved in high-salt-concentration buffer [10 mM Tris-hydrochloride (pH 7.5), 10 mM MgCl$_2$, 1 mM DTT and 100 mM NaCl], 100 units of the restriction enzyme EcoRI and 200 units of the restriction enzyme ScaI were added to the solution and the reaction was carried out at 37° C. for 2 hours.

The reaction mixture was subjected to 1% low-meltingpoint agarose gel electrophoresis and a band of about 0.9 kb was excised. The gel fragment was melted by heating at 65° C. for 5 minutes, phenol was added, the mixture was stirred and then centrifuged. The upper layer was further stirred with phenol-chloroform and then with chloroform, each time followed by centrifugation. To the final upper layer were added one-tenth volume of 3 M sodium acetate and 2.5 volumes of ethanol for ethanol precipitation, which gave the desired DNA fragment. The DNA fragment obtained was treated with 4 units of Klenow fragment in Klenow buffer [50 mM Tris-hydrochloride (pH 7.2), 10 mM MgSO$_4$, 0.1 mM DTT, 50 μg/ml BSA and 0.2 mM dNTP] at 37° C. for 30 minutes. Phenol was added to the reaction mixture, the whole mixture was stirred for enzyme inactivation the upper layer was further treated with chloroform for phenol elimination and finally desalted on Sephadex G-50 to give the desired pSTP1(E-Sc-Klenow) fragment.

The plasmid pUC18 (20 μg) was dissolved in high-salt-concentration buffer [10 mM Tris-hydrochloride (pH 7.5), 10 mM MgCl$_2$, 1 mM DTT and 100 mM NaCl], 100 units of the restriction enzyme PvuII and 100 units of the restriction enzyme ScaI were added to the solution and the reaction was conducted at 37° C. for 2 hours. The reaction mixture was subjected to 1% low-melting-point agarose gel electrophoresis and a band of about 1.5 kb was excised. The gel fragment was melted by heating at 65° C. for 5 minutes, phenol was added, the mixture was stirred, then centrifuged, and the upper layer was further stirred with phenol-chloroform and with chloroform, each time followed by centrifugation. To the final upper layer were added one-tenth volume of 3 M sodium acetate and 2.5 volumes of ethanol for ethanol precipitation, which gave the desired pUC18(P-Sc) fragment.

The two DNA fragments prepared, namely the pSTP1(E-Sc-Klenow) fragment (100 ng) and the pUC18(P-Sc) fragment (500 ng), were ligated to each other by treatment in ligation buffer [66 mM Tris-hydrochloride (pH 7.6), 6.6 mM MgCl₂, 10 mM DTT and 0.1 mM ATP] at 16° C. for 21.5 hours in the presence of 350 units of T4 DNA ligase. The reaction mixture was used to transform *Escherichia coli* RR1ΔM15 in the conventional manner by the Hanahan method. The desired transformant pUCSTP1/RR1ΔM15 was obtained on an L-plate containing 50 μg/ml of ampicillin. The directionality of the inserted gene was confirmed by the patterns of cleavage with the restriction enzymes EcoRI and EcoRI-ScaI.

ii) Preparation of pGMVGH1-trp

The plasmid pUCSTP1 (3 μg) was dissolved in medium-salt-concentration buffer [10 mM Tris-hydrochloride (pH 7.5) 10 mM MgCl₂, 1 mM DTT and 50 mM NaCl], 50 units of the restriction enzyme HindIII was added to the solution and the reaction was conducted at 37° C. for 2 hours. The reaction mixture was subjected to 0.7% low-melting-point agarose gel electrophoresis and a band of about 2.4 kb was excised. The gel fragment was melted by heating at 65° C. for 5 minutes, phenol was added the mixture was stirred and then centrifuged. The upper layer was further stirred with phenol-chloroform and then with chloroform, each time followed by centrifugation. To the final upper layer were added one-tenth volume of 3 M sodium acetate and 2.5 volumes of ethanol for ethanol precipitation, which gave the desired DNA fragment. The DNA fragment obtained was treated with 2 units of alkaline phosphatase in alkaline phosphatase buffer [50 mM Tris-hydrochloride (pH 8.0) and 0.1 mM EDTA] at 37° C. for 1 hour. Phenol was added to the reaction mixture, the whole mixture was stirred for enzyme inactivation, the upper layer was further stirred with phenol-chloroform and then with chloroform, each time followed by centrifugation. The final upper layer was desalted on Sephadex G-50 to give the desired pUCSTP1(H-Alp) fragment.

The plasmid pGMVG1-trp (5 μg) was dissolved in medium-salt-concentration buffer [10 mM Tris-hydrochloride (pH 7.5), 10 mM MgCl₂, 1 mM DTT and 50 mM NaCl], 150 units of the restriction enzyme HindIII was added to the solution and the reaction was conducted at 37° C. for 2 hours. The reaction mixture was subjected to 1% low-melting-point agarose gel electrophoresis and a band of about 1.2 kb was excised. The gel fragment was melted by heating at 65° C. for 5 minutes, phenol was added, the mixture was stirred and then centrifuged. The upper layer was further stirred with phenol-chloroform and with chloroform, each time followed by centrifugation. To the final upper layer were added one-tenth volume of 3 M sodium acetate and 2.5 volumes of ethanol for precipitation, whereby the desired pGMVG1-trp(H) fragment was obtained.

The two DNA fragments prepared, namely the pGMVG1-trp(H) fragment (150 ng) and the pUCSTP1(H-Alp) fragment (80 ng), were ligated to each other by treating in ligation buffer [66 mM Tris-hydrochloride (pH 7.6), 6.6 mM MgCl₂, 10 mM DTT and 0.1 mM ATP]in the presence of 700 units of T4 DNA ligase at 16° C. for 20.5 hours. The ligation reaction mixture was used to transform *Escherichia coli* C600galK⁻ in the conventional manner by the Hanahan method, and the desired transformant of Example 4, pGMVGH1-trp/C600galK⁻ was obtained on an L-plate containing 50 μg/ml of ampicillin and 25 μg/ml of tryptophan. The gene insertion and the directionality thereof were confirmed by cleavage with the restriction enzymes HindIII and BamHI-ScaI in a double digest.

Figure 3:
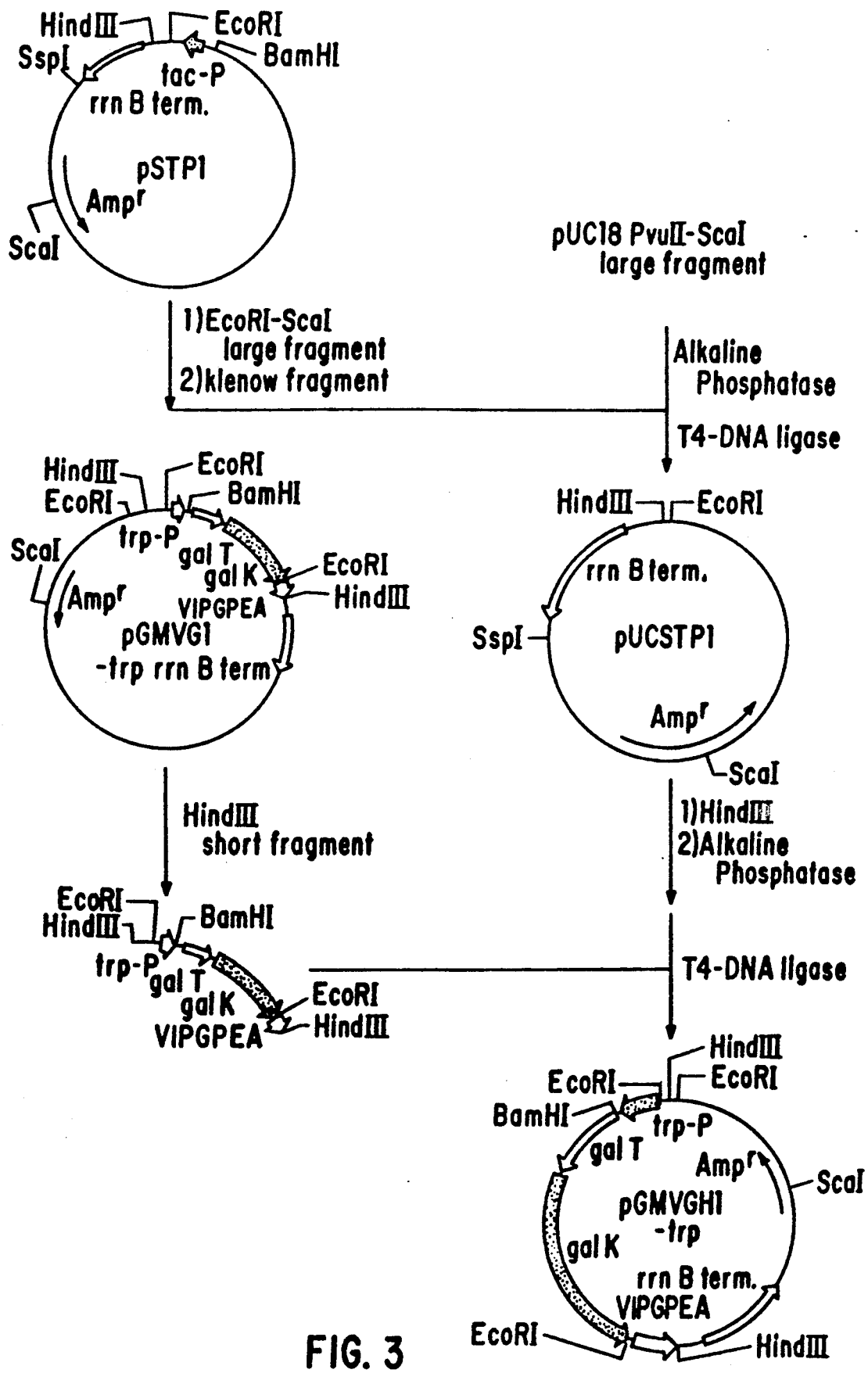
FIG. 3 shows conversion of the plasmid pGMVG1-trp (pBR plasmid) to the plasmid pGMUGH1-trp (pUC plasmid).

The structure of the plasmid pGMVGH1-trp is illustrated in FIG. 3. The Hind III short fragment of the plasmid pGMVG1-trp comprised DNA fragment from the trp promoter through the VIPGPEA-coading gene but not any terminater region. Then, the EcoRI-ScaI fragment of the plasmid pSTP1, comprising the terminator same as that of the plasmid pGMVG1-trp, was incorporated into the plasmid pUC18 to constitute the plasmid pUCSTP1. Furthermore, into the plasmid pUCSTP1 was incorporated the above Hind III short fragment of the plasmid pGMVG1-trp to constitute the plasmid pGMVGH1-trp. The plasmids pGMVG1-trp and pGMVGH1-trp each comprised common structures in terms of trp promoter, gene coading galK-VIPGPEA and terminator, with difference in the base plasmid being a pBR plasmid or a pUC plasmid.

Preparation of pGMVGH1-trp/W3110

The plasmid pGMVGH1-trp extracted from the transformant of Example 4, pGMVGH1-trp/C600galK⁻ was used to transform *Escherichia coli* W3110 in the conventional manner by the Hanahan method, and the desired transformant of Example 5, pGMVGH1-trp/W3110 was obtained on an L-plate containing 50 μg/ml of ampicillin and 100 μg/ml of tryptophan. The plasmid was identified by restriction enzyme cleavage.

(2) Expression and identification of fused proteins

Identification of the fused protein produced in pGMVG1/RR1ΔM15

The recombinant of Example 2, pGMVG1/RR1ΔM15 was cultured overnight at 37° C. in L medium containing 50 μg/ml of ampicillin. A 50-μl portion of the culture fluid was cultured in 10 ml of fresh L medium containing 50 μg/ml of ampicillin at 37° C. When the O.D. 550 (optical density at 550 nm) value reached 0.5 to 0.7, IPTG (isopropyl 1-thio-β-D-galactopyranoside) was added to a final concentration of 1 mM. Cultivation was continued further for 5.5 to 22 hours. A 500-μl portion of the culture fluid was centrifuged. SDS-PAGE buffer was added to the cells thus recovered and, after heating at 95° C. for 5 minutes, 12.5% SDS-PAGE was conducted.

The gel was stained with CBB (Coomassie Brilliant Blue R-250) and then destained, whereby a new band, about 33,000 in molecular weight, was detected.

Separately, the same sample was electrophoresed in the same manner and the gel was subjected to electroblotting onto a nitrocellulose paper. Western blotting was performed with the paper using mouse anti-VIP antisera and alkaline phosphatase-bound anti-mouse IgG, whereby the same band as that detected on CBB staining was singly found to be capable of color development.

It was thus confirmed that the desired peptide had been expressed by the method of the invention in the form of a protein fused to the galK protein, in a proportion of 10–15%.

Identification of the fused protein produced in pGMVG1-trp/C600calK⁻

The recombinant of Example 3, pGMVG1-trp/C600galK⁻ was cultured overnight at 37° C. in L medium containing 50 μg/ml of ampicillin and 2.5 μg/ml of tryptophan and in M9 casamino acid medium. A 50- to 100-μl portion of each culture fluid was added to a fresh 10-ml portion of the corresponding medium containing 50 µg/ml of ampicillin and 2.5 µg/ml of tryptophan and cultivation was conducted at 37° C. When the O.D.550 value reached 0.5 to 0.6, IAA (indoleacrylic acid) was added to a final concentration of 20 µg/ml. After 5 and 23.5 hours of further cultivation, 500 µl of each culture fluid was centrifuged for cell harvesting. SDS-PAGE buffer was added to the cells and, after 5 minutes of heating at 95° C., 12.5% SDS-PAGE was conducted. The gel was subjected to CBB staining followed by destaining, whereupon the same band of about 33,000 in molecular weight as that detected with pGMVG1/RR1ΔM15 as mentioned in the preceding section was detected. The fused protein accounted for 50 to 70% of the total of Escherichia coli proteins.

It was thus confirmed that the desired peptide had been expressed by the method of the invention in large quantities in the form of a protein fused to the galK protein.

Identification of the fused protein produced in pGMVGH1-trp/C600calK⁻

The recombinant of Example 4, pGMVGH1-trp/C600galK⁻ was cultured overnight at 30° C. in high-concentration phosphate casamino acids medium containing 50 µg/ml of ampicillin and 100 µg/ml of tryptophan. A 50-µl portion of the culture fluid was transferred to a fresh 10-ml portion of high-concentration phosphate casamino acids medium containing 50 µg/ml of ampicillin and 100 µg/ml of tryptophan and cultivation was conducted at 30° C. When the O.D.550 value reached about 0.5, the cultivation temperature was raised to 37° C. and cultivation was continued further for 20 hours. A 500-µl portion of the culture fluid thus obtained was centrifuged for cell harvesting. SDS-PAGE buffer was added to the cells and, after 5 minutes of heating at 95° C., 12.5% SDS-PAGE was carried out. The gel was subjected to CBB staining, followed by destaining, whereupon the same band, about 33,000 in molecular weight, as that detected with pGMVG1/RR1ΔM15 as mentioned above was detected. The fused protein accounted for 50 to 70% of the total of Escherichia coli proteins.

It was thus confirmed that the desired peptide had been expressed by the method of the invention in large quantities in the form of a protein fused to the galK protein through temperature shifting from 30° C. to 37° C. without using IAA for induction of protein expression.

Identification of the fused protein produced in pGMVGH1-trp/W3110

The recombinant of Example 5, pGMVGH1-trp/W3110 was cultured overnight at 30° C. in FB-B medium containing 50 µg/ml of ampicillin and 500 µg/ml of tryptophan. A 50-µl portion of the culture fluid was transferred to a fresh portion of FB-B medium containing 50 µg/ml of ampicillin and 500 µg/ml of tryptophan and cultivation was conducted at 30° C. When the O.D.550 value reached about 0.5, the cultivation temperature was raised to 37° C. and cultivation was further continued for 23 hours. A 500-µl portion of the culture fluid was centrifuged for cell harvesting, SDS-PAGE buffer was added to the cells and, after 5 minutes of heating at 95° C., 12.5% SDS-PAGE was performed. The gel was stained with CBB and then destained whereupon the same band, about 33,000 in molecular weight, as that detected with pGMVG1/RR1ΔM15 as mentioned above was detected. The fused protein was found to account for 50 to 70% of the total of Escherichia coli proteins.

It was thus confirmed that, even in Escherichia coli W3110, a strain different from C600galK⁻, the desired peptide had been expressed by the method of the invention in the form of a protein fused to the galK protein in large quantities through temperature shifting from 30° C. to 37° C. without using IAA for induction of protein expression.

(3) Production of peptide VIPGPEA (17-(L)-VIPGPEA)

Production and purification of VIPGPEA

The recombinant Example 3, pGMVG1-trp/C600galK⁻ was cultured overnight at 37° C. in high-concentration phosphate-casamino acids medium containing 50 µg/ml of ampicillin and 25 µg/ml of tryptophan. The culture fluid (70 ml) was transferred to a 10-liter fermenter containing 7 liters of high-concentration phosphate-casamino acids medium containing 50 µg/ml of ampicillin and cultivation was performed at 37° C. When the O.D.550 value reached about 0.5, IAA was added to a final concentration of 20 µg/ml and cultivation was further continued overnight. Cells (wet weight 48.3 g) were recovered by centrifugation (x 8,000 g, 4° C., 15 minutes) of the culture fluid.

The cells recovered were suspended in about 250 ml of cell disruption buffer [10 mM Tris-hydrochloride (pH 8.0) and 1 mM $MgCl_2$] and disrupted using a high-pressure homogenizer (Minilabo) (6,000 psi, ×5 times). The cell disruption mixture was centrifuged (15,400×g, 4° C., 30 minutes). The soluble fraction and insoluble fraction thus separated were analyzed by SDS-PAGE, whereby it was confirmed that the desired fused protein was present in the insoluble fraction. The insoluble fraction (19.4 g in wet weight, derived from 6 liters of culture fluid) was dissolved in 400 ml of 70% formic acid, then 12.4 g of cyanogen bromide was added and the mixture was stirred at room temperature for 44 hours. The reaction mixture was concentrated under reduced pressure in an evaporator, the concentrate was diluted with water and lyophilized. The lyophilizate powder (8.3 g) was suspended in 400 ml of 6 M urea/100 mM phosphoric acid (pH 6.5), the suspension was diluted with three volumes of water and the soluble fractions was recovered by centrifugation (5,000×g, 4° C., 10 minutes).

The soluble fraction (about 1.6 liters) was adjusted to a phosphoric acid concentration of 40 mM and then purified on S-Sepharose Fast Flow column (SS-FF, mfd. by Pharmacia Co., 5 cmφ×8 cm) on a NaCl concentration gradient of 0 to 0.5M. The column fraction (about 400 ml) containing VIPGPEA was desalted and concentrated using a reversed-phase column 1.6 cmφ×10 cm, YMC, type AM, 10 µm in grain size, 120 angstroms in pore size, C18) and then subjected to reversed-phase high-performance liquid chromatography (YMC-AM324) on a 25–35% acetonitrile concentration gradient for separation and purification. Purified 17-(L)-VIP-GPEA was thus obtained in a yield of 160.2 g (purity 99.6%).

The amino acid sequence of the above product was ascertained using a peptide sequencer as H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-Glu-Ala-OH (SEQ ID No: 1).

EXAMPLE 6

Fed-batch fermentation using
pGMVG1-trp/C600galK⁻

The recombinant of Example 3, pGMVG1-trp/C600galK⁻ was cultured overnight at 30° C. in FB-B medium containing 0.1 g/liter of ampicillin, 0.1 g/liter of tryptophan, 0.5 g/liter of leucine, 3 g/liter of threonine and 0.1 g/liter of thiamine hydrochloride. The culture fluid (500 ml) was transferred to a 10-liter fermenter containing 5 liters of FB-B medium that included 0.05 g/liter of ampicillin, 0.3 g/liter of tryptophan, 1 g/liter of leucine, 6 g/liter of threonine and 0.1 g/liter of thiamine hydrochloride and cultivation was conducted at 37° C. The speed of rotation for stirring was controlled within the range of 200–900 rpm and the rate of aeration within the range of 5–15 liters/min. to assure maximum aeration. The pH of the culture fluid was adjusted routinely to 7.0 with 5 M NaOH. Gradual addition of FB-F medium containing 0.1 g/liter of ampicillin, 1 g/liter of tryptophan, 5 g/liter of leucine, 30 g/liter of threonine and 0.1 g/liter of thiamine hydrochloride was started at 3 hours after commencement of cultivation. The cultivation was continued while monitoring from time to time the turbidity (O. D.550) of culture fluid, the glucose concentration in medium and the concentration of acetate formed. At 9.5 hours after initiation of cultivation, 0.5 g of IAA was added followed by further cultivation. The cultivation was completed at 14 hours after initiation of cultivation. Cultured cells were harvested by centrifugation (8,000×g, 10 minutes, 4° C.) (total wet cell weight 751 g, dried weight 23 g/liter).

SDS-PAGE buffer was added to a portion of cultured cells at each hour of cultivation and, after 5 minutes of heating at 95° C., 12.5% SDS-PAGE was carried out, followed by staining with CBB. It was confirmed that the fused protein had been expressed in a proportion of 40–60% in 14 hours.

EXAMPLE 7

Fed-batch fermentation using pGMVGH1-trp/W3110

The recombinant of Example 5, pGMVGH1-trp/W3110 was cultured overnight at 30° C. in FB-B medium containing 0.1 g/liter of ampicillin and 0.5 g/liter of tryptophan. The culture fluid (500 ml) was transferred to a 10-liter fermenter containing 5 liters of FB-B medium that included 0.05 g/liter of ampicillin and 1 g/liter of tryptophan and cultivation was carried out at 30° C. The speed of rotation for stirring was controlled within the range of 200–900 rpm and the rate of aeration within the range of 5–15 liters/min. to assure maximum aeration. The pH of the culture fluid was adjusted to 7.0 with 10 M NaOH. At 6.1 hours after commencement of cultivation, gradual addition of FB-F medium containing 0.1 g/liter of ampicillin and 5 g/liter of tryptophan was started. The cultivation was continued while monitoring from time to time the turbidity (O.D.550) of culture fluid, the glucose concentration in medium and the concentration of acetate formed. At 8.8–9.4 hours after initiation of cultivation, the culture temperature was raised from 30° C. to 37° C. and the cultivation was further continued. At 13 hours from commencement of cultivation, the cultivation was completed. Cultured cells were harvested by centrifugation (8,000×g, 10 minutes, 4° C.) (total wet weight 217 g, dried weight 9.6 g/liter).

SDS-PAGE buffer was added to a portion of cultured cells at each hour of cultivation and, after 5 minutes of heating at 95° C., 12.5% SDS-PAGE was performed, which was followed by CBB staining. It was confirmed that, at hour 13, the fused protein had been expressed in a proportion of not less than 60%. It was also confirmed that the expression can be efficiently induced by raising the cultivation temperature from 30° C. to 37° C.

| L-medium | |
|---|---|
| Tryptone | 10 g |
| Yeast extract | 5 g |
| NaCl | 5 g |
| total | 1000 ml |
| M9 Casamino acids medium | |
| $Na_2HPO_4$ | 6 g |
| $KH_2PO_4$ | 3 g |
| NaCl | 0.5 g |
| $NH_4Cl$ | 1 g |
| $CaCl_2$ | 0.01 g |
| $MgSO_4$ | 0.24 g |
| Glucose | 6 g |
| Casamino acids | 5 g |
| Thiamine hydrochloride | 0.1 g |
| total | 1000 ml |
| High-concentration phosphate-casamino acids medium | |
| $MgSO_4.7H_2O$ | 0.4 g |
| $CaCl_2$ | 0.01 g |
| $FeSO_4.7H_2O$ | 0.005 g |
| Sodium citrate | 1 g |
| $KH_2PO_4$ | 5.4 g |
| $K_2HPO_4$ | 36.6 g |
| $(NH_4)_2SO_4$ | 4 g |
| Glucose | 10 g |
| Casamino acids | 5 g |
| total | 1000 ml |
| FB-B medium | |
| $MgSO_4.7H_2O$ | 1 g |
| $KH_2PO_4$ | 8 g |
| $K_2HPO_4$ | 7 g |
| $(NH_4)_2SO_4$ | 5 g |
| Glucose | 5 g |
| Yeast extract | 5 g |
| $CaCl_2.2H_2O$ | 0.006 g |
| $FeCl_3.6H_2O$ | 0.09 g |
| $ZnCl_2.4H_2O$ | 0.004 g |
| $NaMoO_4.2H_2O$ | 0.004 g |
| $CuSO_4.5H_2O$ | 0.004 g |
| $H_3BO_4$ | 0.001 g |
| total | 1000 ml |
| FB-F medium | |
| $MgSO_4.7H_2O$ | 8.5 g |
| $(NH_4)_2SO_4$ | 80 g |
| Glucose | 433 g |
| $CaCl_2.2H_2O$ | 0.17 g |
| $FeCl_3.6H_2O$ | 2.52 g |
| $ZnCl_2.4H_2O$ | 0.11 g |
| $NaMoO_4.2H_2O$ | 0.11 g |
| $CuSO_4.5H_2O$ | 0.11 g |
| $H_3BO_4$ | 0.03 g |
| total | 1000 ml |

While the invention has been described in detail and with reference to specific examples thereof, it will be apparent to one skilled in the art that various changes and modifications can be made therein without departing from the spirit and scope thereof.

What is claimed is:

1. A method of producing a peptide having no L-methionine residue and having a molecular weight of 2,000 to 10,000, comprising;

(A) cultivating prokaryotic cells carrying a recombinant pUC plasmid which contains a trp promoter and a DNA coding for a fused protein, said fused protein comprising;
  (1) a galK protein fragment comprising 200 to 300 amino acid residues from the N terminus of the galK protein, and
  (2) an L-methionine-free peptide having a molecular weight of 2,000 to 10,000 coupled to said galK protein fragment at the C terminus thereof via an L-methionine residue;
to cause expression of said fused protein;
(B) purifying said fused protein;
(C) cleaving said purified fused protein with cyanogen bromide to yield a peptide mixture; and
(D) isolating peptides which have a molecular weight of 2,000 to 10,000 from the peptide mixture to obtain said peptide having no L-methionine residue.

2. The method as claimed in claim 1, wherein the peptide having no L-methionine residue in the molecule and having a molecular weight of 2,000 to 10,000 has an amino acid sequence selected from the group consisting of:
  (a) H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-Glu-Ala-OH (SEQ ID No: 1);
  (b) H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-Glu-OH (SEQ ID No: 2); and
  (c) H-His-Ser-Asp-Ala-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-Gly-Pro-OH (SEQ ID No: 3).

3. The method as claimed in claim 1, wherein the expressing step (A) is effected by using a fed-batch fermentation method.

4. A recombinant pUC plasmid comprising a trp promoter and a DNA coding for a fused protein, said fused protein comprising:
  (1) a galK protein fragment comprising 200 to 300 amino acid residues from the N terminus of galK; and
  (2) an L-methionine-free peptide having a molecular weight of 2,000 to 10,000 coupled to said galK protein fragment at the C terminus thereof via an L-methionine residue.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
His Ser Asp Ala Val Phe Thr Asp Asn Tyr Thr Arg Leu Arg Lys Gln
 1               5                  10                  15
Leu Ala Val Lys Lys Tyr Leu Asn Ser Ile Leu Asn Gly Pro Glu Ala
            20                  25                  30
```

( 2 ) INFORMATION FOR SEQ ID NO:2:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
His Ser Asp Ala Val Phe Thr Asp Asn Tyr Thr Arg Leu Arg Lys Gln
 1               5                  10                  15
Leu Ala Val Lys Lys Tyr Leu Asn Ser Ile Leu Asn Gly Pro Glu
            20                  25                  30
```

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
His Ser Asp Ala Val Phe Thr Asp Asn Tyr Thr Arg Leu Arg Lys Gln
 1               5                  10                  15
Leu Ala Val Lys Lys Tyr Leu Asn Ser Ile Leu Asn Gly Pro
            20                  25                  30
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AATTCATGCA CTCTGACG                                          18

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:5:

CAGTGAATAC AGCGTCAGAG TGCATG                                                    26

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

CTGTATTCAC TGACAACTAC ACTCGTC                                                   27

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:7:

TGTTTACGCA GACGAGTGTA GTTGT                                                     25

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:8:

TGCGTAAACA GCTGGCAGTT AAG                                                       23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:9:

TCAGGTATTT CTTAACTGCC AGC                                                       23

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

AAATACCTGA ACTCTATCCT GAACGGTCCG GA                                             32

(2) INFORMATION FOR SEQ ID NO:11:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

AGCTTCCGGA CCGTTCAGGA TAGAGT    26

( 2 ) INFORMATION FOR SEQ ID NO:12:

( i ) SEQUENCE CHARACTERISTICS:
        ( A ) LENGTH: 98 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

AATTCATGCA CTCTGACGCT GTATTCACTG ACAACTACAC TCGTCTGCGT AAACAGCTGG    60

CAGTTAAGAA ATACCTGAAC TCTATCCTGA ACTGATAG    98

( 2 ) INFORMATION FOR SEQ ID NO:13:

( i ) SEQUENCE CHARACTERISTICS:
        ( A ) LENGTH: 98 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

GATCCTATCA GTTCAGGATA GAGTTCAGGT ATTTCTTAAC TGCCAGCTGT TTACGCAGAC    60

GAGTGTAGTT GTCAGTGAAT ACAGCGTCAG AGTGCATG    98

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AATTCAGATC TCAAGCTTAA GTGACTAG    28

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AGCTCTAGTC ACTTAAGCTT GAGATCTG    28